(12) United States Patent
Yavuz (10) Patent No.: US 6,256,370 B1
(45) Date of Patent: Jul. 3, 2001

(54) METHOD AND APPARATUS FOR PERFORMING TOMOSYNTHESIS

(75) Inventor: Mehmet Yavuz, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/489,896

(22) Filed: Jan. 24, 2000

(51) Int. Cl.$^7$ ........................................... A61B 6/03
(52) U.S. Cl. .................................. 378/22; 378/4; 378/901
(58) Field of Search .............................. 378/4, 15, 2, 22, 378/901

(56) References Cited

U.S. PATENT DOCUMENTS

| | | | |
|---|---|---|---|
| 5,214,686 | * | 5/1993 | Webber ................................. 378/38 |
| 5,859,893 | * | 1/1999 | Moorman et al. .................... 378/154 |

OTHER PUBLICATIONS

"Practical Cone–Beam Algorithm", by L. Feldkamp et al, J. Opt. Soc. Am., a/vol. 1, No. 6, Jun 1984.
"Principles of Computerized Tomographic Imaging", by A. Kak et al, IEEE Press, New York, pp. 99–112.
Copending U.S. application No. 09/409,889 filed Oct. 1, 1999, by Ralph A. Hewes et al., entitled "Apparatus and Method for Obtaining X–Ray Tomosynthesis Data for Mammography".
Copending U.S. application No. 09/448,353, filed Nov. 23, 1999, by Peter M. Edic et al., entitled "Mathematical Model and a Method and Apparatus for Utilizing the Model".
Copending U.S. application No. 09/360,537, filed Jul. 26, 1999, by Mehmet Yavuz et al., entitled "A Method and Apparatus for Reconstructing Image Data Acquired by a Tomosynthesis X–Ray Imaging System".
Copending U.S. application No. 09/585,786, filed Jun. 5, 2000, by Peter M. Edic et al., entitled "Apparatus, Methods, and Computer Programs for Estimating and Correcting Scatter in Digital Radiographic and Tomographic Imaging".

* cited by examiner

Primary Examiner—David V. Bruce
(74) Attorney, Agent, or Firm—Douglas S. Ingraham; Douglas E. Stoner (57) ABSTRACT

A method and an apparatus are provided that enable x-ray projection data acquired by a tomosynthesis system to be transformed into a form as if it had been acquired by a computed tomography (CT) detector. As the x-ray projection data is acquired by a tomosynthesis detector of the tomosynthesis system, the projection data is projected onto a virtual CT detector. The transformed data is then processed to associate virtual pixels of the virtual CT detector with coordinates on the tomosynthesis detector. The intensity values of the pixels of the tomosynthesis detector are then used to interpolate the intensity values of the corresponding virtual pixels of the virtual CT detector. The intensity values of the virtual pixels of the virtual CT detector may then be processed in accordance with a CT reconstruction algorithm to reconstruct the image. Thus, the present invention enables CT reconstruction algorithms to be used to reconstruct data acquired by a tomosynthesis system, which greatly improves the quality of images reconstructed from image data acquired by a tomosynthesis system.

24 Claims, 6 Drawing Sheets

METHOD AND APPARATUS FOR PERFORMING TOMOSYNTHESIS

BACKGROUND OF THE INVENTION

This invention relates to tomosynthesis and, more particularly, to a method and apparatus for performing tomosynthesis by acquiring 2-D x-ray projection images of an object, transforming the data into a form as if it had been acquired by a computed tomography (CT) system, and then reconstructing a 3-D representation of the object by utilizing a CT image reconstruction algorithm. By utilizing a CT reconstruction algorithm to reconstruct an image from image data acquired by a tomosynthesis system, the quality of the reconstructed images is greatly improved.

Digital tomosynthesis enables a three dimensional (3-D) image of an object to be constructed from a finite set of two-dimensional (2-D) projection radiograph images. The system comprises an x-ray source and a 2-D x-ray detector, which is a digital detector. In typical digital tomosynthesis systems, during data acquisition, the x-ray source is rotated by a gantry on an arc through a limited angular range about a pivot point and a set of projection radiographs of the object are acquired by the detector at discrete locations of the x-ray source. The detector is maintained at a stationary position as the radiographs are acquired.

Once the projection radiographs have been obtained, they are then spatially translated with respect to each other and superimposed in such a manner that the images of structures in the tomosynthesis plane overlap exactly. The images of structures outside the tomosynthesis plane do not overlap exactly, resulting in a depth dependent blurring of these structures. By varying the amount of relative translation of the projection radiographs, the location of the tomosynthesis plane can be varied within the object. Each time the tomosynthesis plane is varied, the image data corresponding to the overlapping structures is superimposed and a 2-D image of the structure in the tomosynthesis plane is obtained. Once a complete set of 2-D images of the object has been obtained, a 3-D image of the object is generated from the set of 2-D images.

Computed tomography (CT) is a technique that generally involves subjecting a patient to x-rays, acquiring digital x-ray data of a portion of the patient's body, and processing and back-projecting the digital x-ray data to construct a 3-D image of the object. The image may then be displayed on a display monitor of the CT system. CT systems typically comprise a gantry, a table, an x-ray tube, an x-ray detector array, a computer and a display monitor. The computer sends commands to controllers of the gantry to cause the controllers to rotate the x-ray tube and/or the detector array at a particular rotational speed to produce relative rotation between the x-ray tube and the detector array 360° about the patient. The detector array is usually comprised of either a curved array (third generation CT system) of detector elements or a ring (fourth generation CT system) of detector elements. In the case where a ring of detector elements is used, only the x-ray tube is rotated.

As stated above, in digital tomosynthesis, the acquired projection radiographs are spatially translated and superimposed such that the structures in the tomosynthesis plane overlap. The images of structures outside of the tomosynthesis plane do not coincide precisely when they are superimposed, which results in a depth dependent blurring of these structures. These out-of-plane structures are superimposed into the reconstructed plane, which degrades the overall reconstructed image quality and results in relatively low depth resolution. In contrast, the filtered back projection reconstruction algorithms utilized by CT systems to reconstruct a 3-D image from acquired 2-D image slices generally produces reconstructed images of much higher quality and better depth resolution than the reconstructed images produced by using digital tomosynthesis systems.

It would be desirable to provide a digital tomosynthesis system that could perform reconstruction using a filtered back projection algorithm such as that used in CT systems. However, due to the differences between digital tomosynthesis and CT geometries, image reconstruction algorithms that are normally utilized by CT systems generally are not suitable for tomosynthesis reconstruction. Accordingly, a need exists for a digital tomosynthesis system that is capable of utilizing image reconstruction algorithms of the type typically used with CT systems to perform reconstruction.

BRIEF SUMMARY OF THE INVENTION

The present invention provides a method and an apparatus that enable x-ray projection data acquired by a tomosynthesis system to be transformed into a form as if it had been acquired by a computed tomography (CT) detector of a CT system. As the x-ray projection data is acquired by the tomosynthesis detector of the tomosynthesis system, the projection data is projected onto a virtual CT detector. The transformed data is then processed to associate virtual pixels of the virtual CT detector with coordinates on the tomosynthesis detector. The intensity values of the pixels of the tomosynthesis detector are then interpolated to compute the intensity values of the corresponding virtual pixels of the virtual CT detector. The intensity values of the virtual pixels of the virtual CT detector may then be processed in accordance with a CT reconstruction algorithm to reconstruct the image. Thus, the present invention enables CT reconstruction algorithms to be used to reconstruct images acquired by a tomosynthesis system.

These and other features of the present invention will become apparent from the following description, drawings and claims.

DETAILED DESCRIPTION OF THE INVENTION

Figure 1:
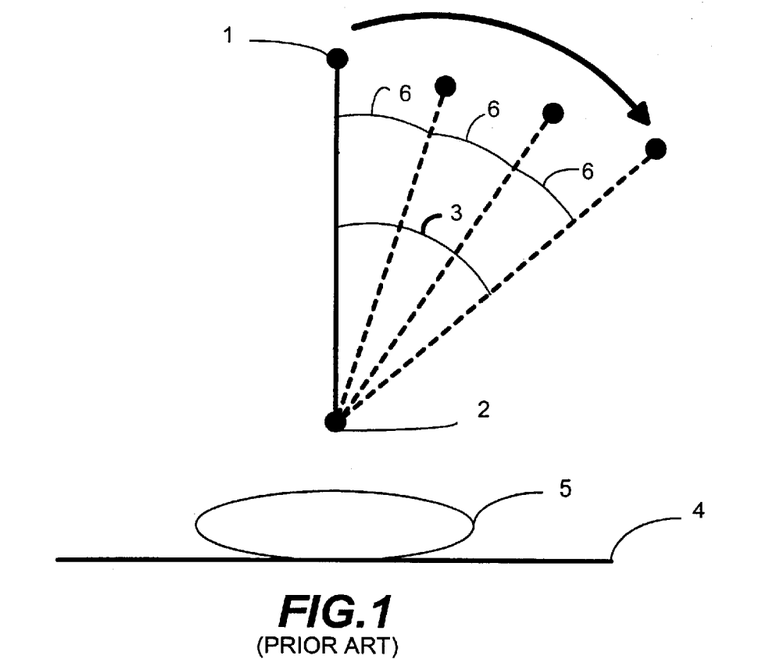
FIG. 1 is an illustration of the system geometry of a typical tomosynthesis system.

FIG. 1 illustrates the system geometry of a typical digital tomosynthesis system. The x-ray source 1 is rotated on an arc about a pivot point 2 through a particular angular range, which is represented by the numeral 3. At discrete locations along the arc, the digital detector 4 acquires projection radiographs associated with x-rays that pass through the object being imaged 5 and impinge on the detector 4. The discrete locations of the source 1 along the arc correspond to incremental rotations of the source 1 through angles 6 that make up the angular range 3. As stated above, once the projection radiographs have been acquired, they are spatially translated with respect to each other and superimposed such that the structures in the tomosynthesis plane precisely overlap, whereby a 3-D reconstructed image is produced. In some tomosynthesis systems, the detector 4 is moved horizontally in a direction away from the source as the source 1 is rotated. In some tomosynthesis systems, the source 1 is moved horizontally rather than rotationally and the detector 4 is either kept stationary or is moved horizontally in a direction away from the source as the source 1 is rotated.

Figure 2:
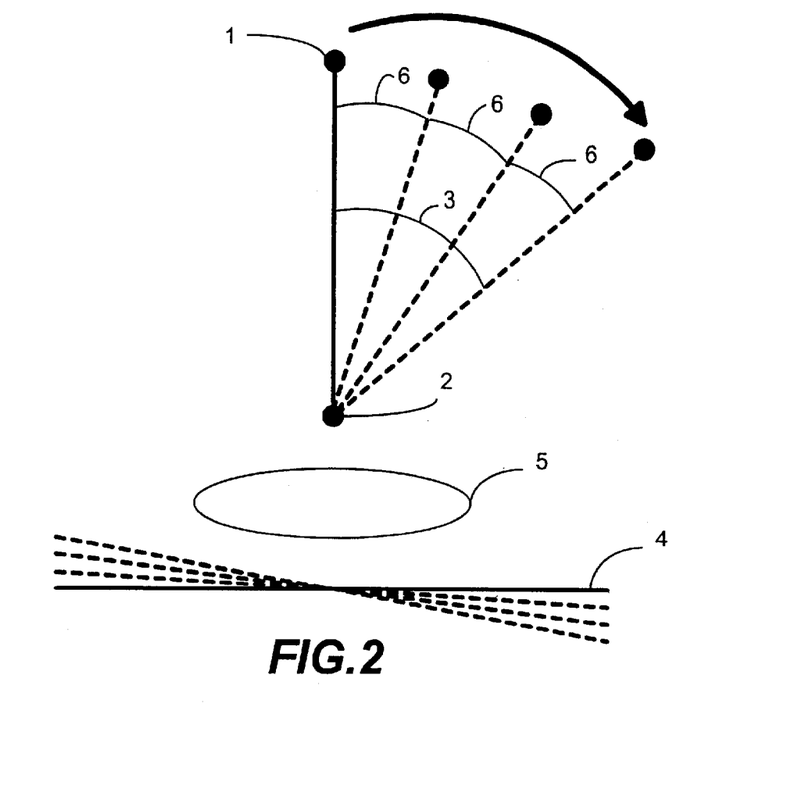
FIG. 2 is an illustration of a tomosynthesis system geometry that has been transformed in accordance with the method of the present invention.

The present invention is directed to a method and apparatus that can be incorporated into a digital tomosynthesis system to enable CT back projection reconstruction algorithms to be utilized to reconstruct the image of the object 5. FIG. 2 illustrates the geometry of the transformed tomosynthesis system of the present invention. The geometry of the tomosynthesis system shown in FIG. 2 is identical to the geometry of the tomosynthesis system shown in FIG. 1 except that the data acquired by the detector 4 is transformed into a form that would result if rotational motion of the detector 4 and the source 1 was produced. This transformation is represented by the dashed lines below the object 5, which are intended to represent motion of the detector 4 in synchronization with the motion of the source 1. It should be noted that motion may be imparted only to the source 1 or to both the source and detector 4, as discussed above with respect to FIG. 1. In either case, the transformation algorithm of the present invention will enable a CT reconstruction algorithm to be utilized to reconstruct the image, as discussed below in detail.

The transformation of the present invention converts the projection radiographs collected by the detector 4 into projection radiographs that are of the type normally acquired by CT systems. The transformed projection data may then be processed using a filtered back projection reconstruction algorithm as in CT. By reconstructing the image in this manner, the aforementioned problems associated with typical tomosynthesis reconstruction are reduced or eliminated. However, since these CT back projection reconstruction algorithms are normally used with projection radiographs acquired through 360° of relative rotation between the source 1 and the detector 4, the CT back projection reconstruction algorithm that is utilized with the tomosynthesis system of the present invention must be modified to account for the limited angular range of rotation of the source. Prior to discussing the transformation algorithm of the present invention, the components of the tomosynthesis system of the present invention will be described with reference to FIG. 3.

Figure 3:
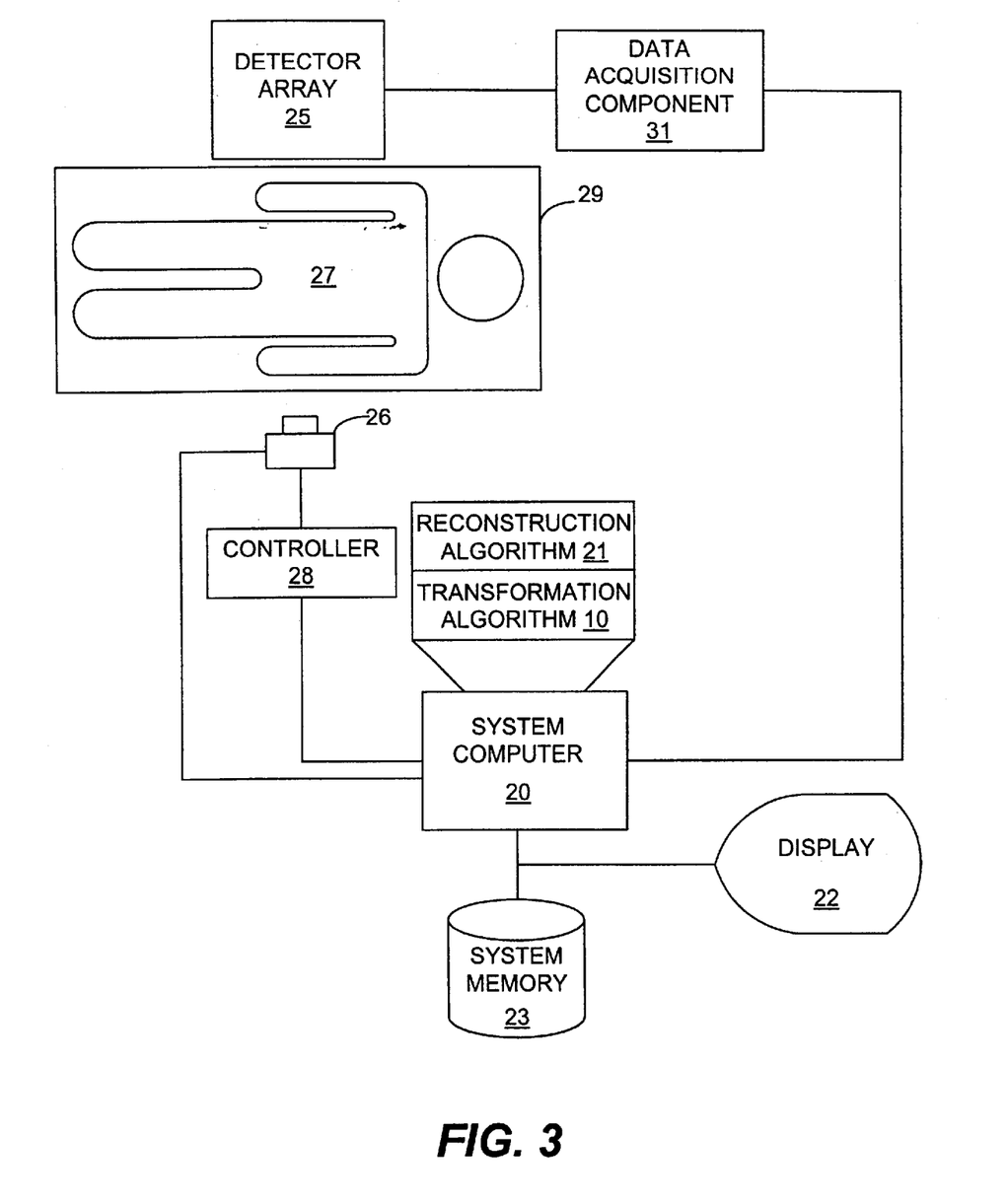
FIG. 3 is a block diagram of the tomosynthesis system of the invention in accordance with the preferred embodiment.

FIG. 3 is a block diagram of the tomosynthesis system of the present invention in accordance with the preferred embodiment. The tomosynthesis system has the system geometry represented by FIG. 2. However, in contrast to typical tomosynthesis systems, a transformation algorithm 10 executed by the computer 20 transforms the projection data collected by the digital tomosynthesis system into projection data of the type normally collected by computed tomography (CT) systems. Once the transformation algorithm 10 executed by the computer 20 has transformed the image data acquired by the tomosynthesis system, a filtered back projection reconstruction algorithm 21 executed by the computer 20 reconstructs the image. The transformation algorithm 10 and the reconstruction algorithm 21 will be discussed below in detail with reference to FIGS. 4–8.

The computer 20 is in communication with a display 22 and with a system data storage component 23. The system data storage component 23 stores data utilized by the computer 20 to perform its tasks. The system data storage component 23 also stores image data that has been acquired by the tomosynthesis system. In addition, the system data storage component 23 may store the code corresponding to the algorithms 10 and 21, as well as images that have been reconstructed by those algorithms. The computer 20 is capable of causing reconstructed images to be displayed on the display device 22.

The tomosynthesis system of the present invention preferably comprises a digital detector 25 and an x-ray source 26 for projecting x-rays through the object being imaged 27, which may be a human patient, for example. A table 29 supports the patient. The detector 25 receives x-rays that pass through the object 27 and generates digital signals related to the intensity of the x-rays. The x-ray source 26 is in communication with a controller 28, which is in communication with the computer 20. The computer 20 outputs instructions to the controller 28. In response to receiving the instructions from the computer 20, the controller 28 moves a gantry (not shown) that moves the source 26 along an arcuate trajectory through a particular range of viewing angles, as discussed above with reference to FIGS. 1 and 2.

At particular locations of the source 26 along the arcuate trajectory, image samples are acquired by the detector 25. The detector 25, which preferably is a digital detector, generates digital voltage signals in response to the x-rays impinging thereon. It should be noted that an analog detector could also be used, such as an image intensifier. If an analog detector is used, the acquired analog voltage signals will be converted into digital voltage signals. The digital voltage signals are provided to the computer 20 for processing by a data acquisition component 31. If an image intensifier is used as the detector 25, the data acquisition component will digitize the analog signals as it reads them out of the image intensifier.

Figure 4:
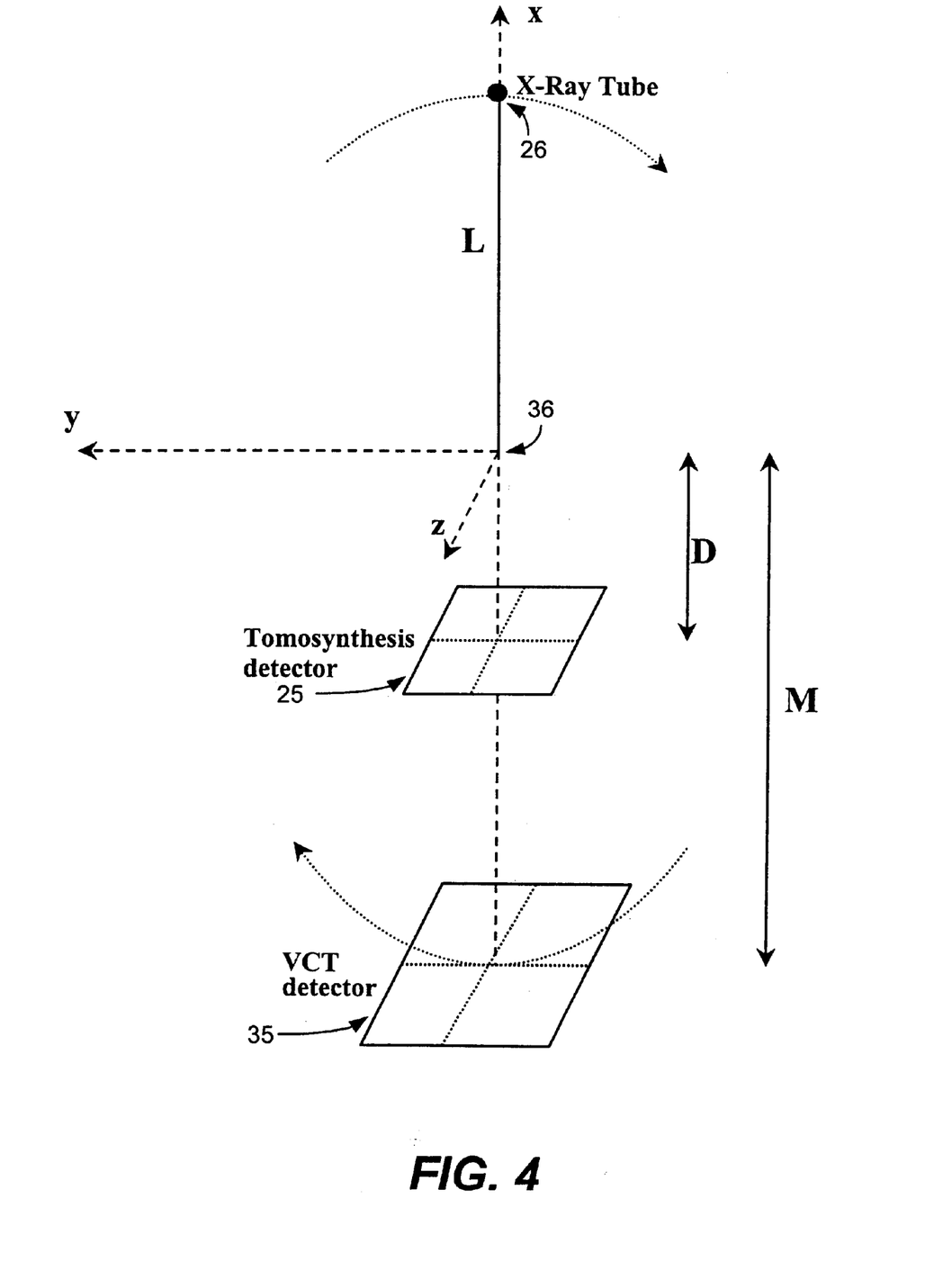
FIG. 4 is a diagram illustrating the relationship between the tomosynthesis detector of the system shown in FIG. 3 and a virtual VCT detector that is utilized in performing the method of the present invention.

The manner in which the transformation algorithm 10 transforms the tomosynthesis projection data will now be described with reference to FIGS. 4–8. For purposes of illustration, it will be assumed that only the x-ray source 26 is moved and that it is moved rotationally (as opposed to linearly) with respect to the object 27. However, it should be noted that the source 26 and the detector 25 could be moved in any of the manners discussed above with reference to FIG. 1, and that the method and apparatus of the present invention equally apply to these situations. The X-ray tube 26 is rotated on a gantry of length L, as shown in FIG. 4. During the operation of the tomosynthesis system, X-ray projection images are acquired at discrete locations of the tube 26 during the rotation. The digital tomosynthesis detector 25 is located a distance D below the pivot point 36.

In accordance with the present invention, the projection data acquired by the tomosynthesis detector 25 is projected onto a virtual detector 35, which will be referred to herein as a virtual Volumetric Computed Tomography (VCT) detector. This virtual VCT detector 35 is located a distance M from the pivot point 36. The virtual VCT detector 35 is assumed to be rotated around the pivot point in an opposite direction to the direction of rotation of the X-ray tube 26. Of course, the virtual VCT detector 35 is not physically rotated, but rather, is algorithmically manipulated.

Figure 5:
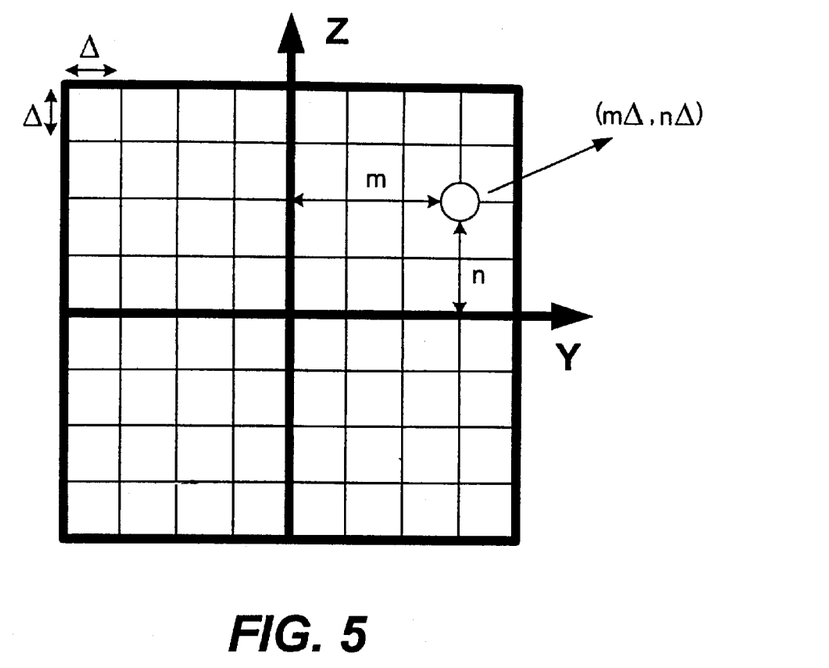
FIGS. 5 and 6 illustrate the coordinate systems of the tomosynthesis detector and of the virtual VCT detector shown in FIG. 4.

The tomosynthesis detector 25 collects X-ray projection images on a discrete grid of pixels, as shown in FIG. 5. The pitch between the detector pixels is denoted herein as "$\Delta$". Using the pitch, the (y, z) coordinates of each pixel are given as follows. For a pixel that is "m" number of pixels away from the origin in the "y" direction and "n" number of pixels away from origin in "z" direction, the corresponding (y, z) coordinates are (m$\Delta$, n$\Delta$).

Figure 6:
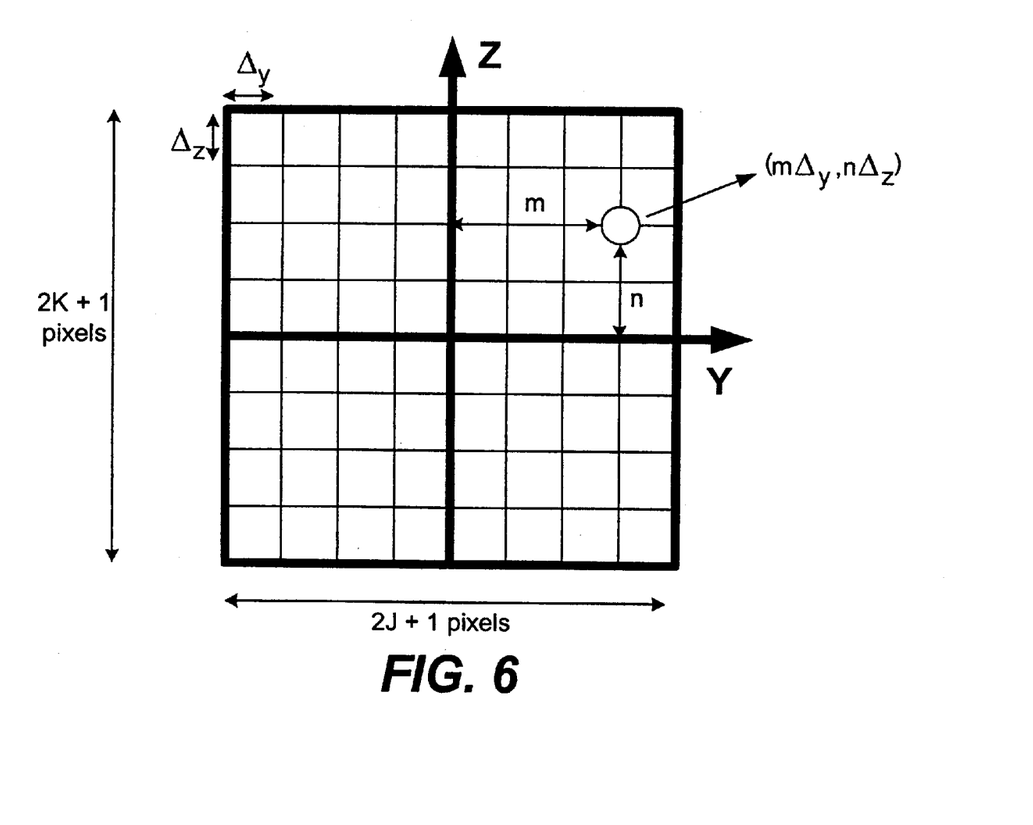

The (y, z) coordinates of each pixel on the virtual VCT detector 35 can be derived in a similar manner, as demonstrated by FIG. 6. The pixel pitch in the "y" and "z" directions is denoted by $\Delta_y$ and $\Delta_z$, respectively. For a pixel that is "m" number of pixels away from the origin in the "y" direction and "n" number of pixels away from origin in "z" direction, the corresponding (y, z) coordinates are (m$\Delta_y$, n$\Delta_z$).

Having described the coordinate systems associated with the tomosynthesis detector 25 and the virtual VCT detector 35, the algorithm 10 that performs the transformation of the projection data into intensity values of the virtual vertical detector 35 will now be described. This transformation process is demonstrated by FIG. 7, which shows the rotation of the source 26 and the virtual VCT detector 35. The tomosynthesis detector 25 remains stationary. As mentioned above, the X-ray tube 26 is rotated by the gantry around the pivot point 36 and N separate X-ray projection images are collected at discrete gantry angles $\theta_j$, for i=1, . . . , N. Each projection image acquired by the tomosynthesis detector is transformed onto the virtual VCT detector 35.

Figure 7:
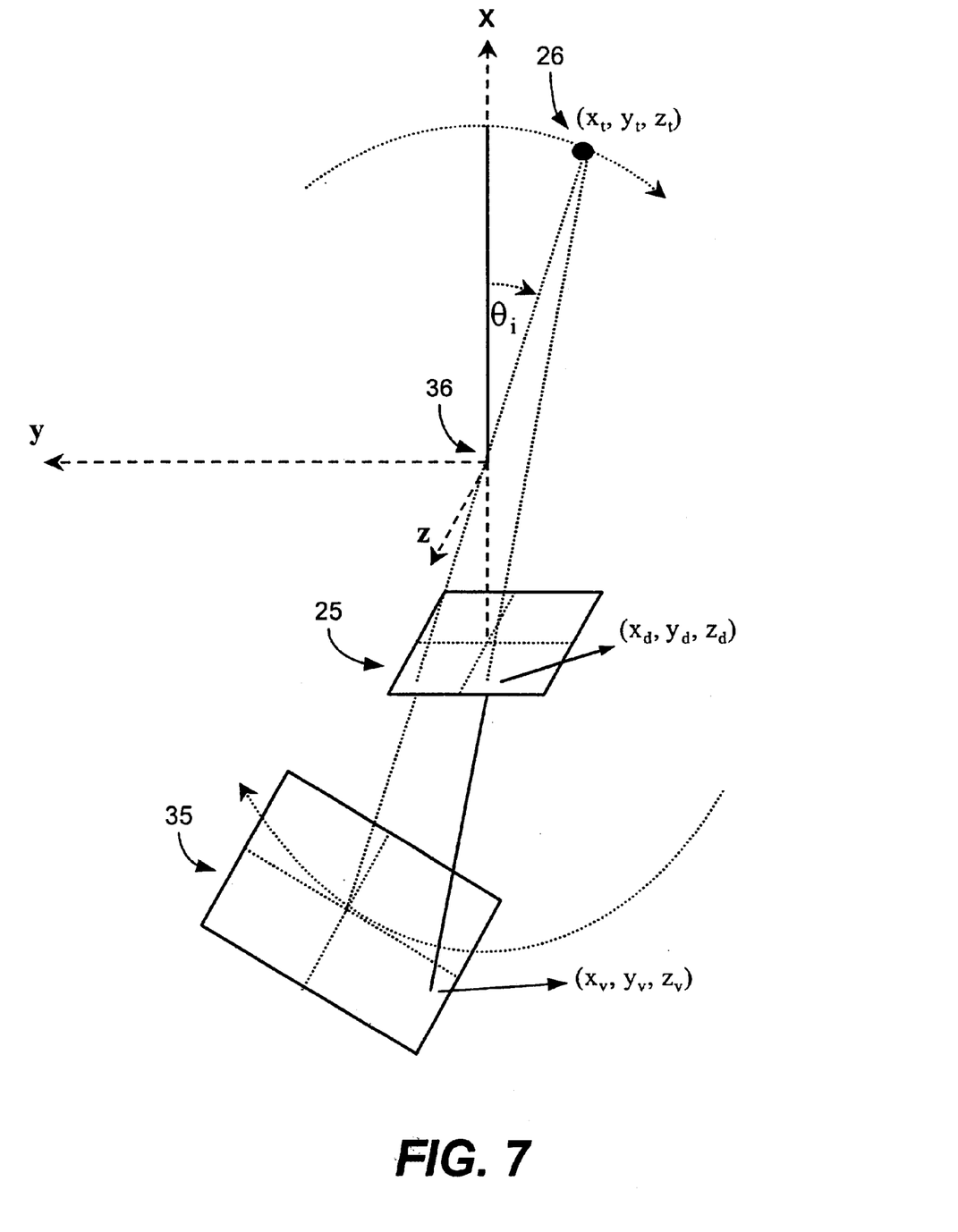
FIG. 7 is a diagram illustrating the relationship between the tomosynthesis detector and virtual VCT detector shown in FIG. 4 when motion is imparted to the virtual VCT detector.

A coordinate location ($X_d$, $y_d$, $z_d$) on the tomosynthesis detector 25 corresponds to a coordinate location ($x_v$, $y_v$, $z_v$) on the virtual VCT detector 35. For each X-ray tube position of $\theta_j$, 1, . . . , N), the coordinates of the tube location are computed as:

$$x_s = L \cos(-\theta_j)$$

$$y_s = L \sin(-\theta_j)$$

$$z_s = 0$$

The coordinates of the pixels of the virtual vertical detector 35 are then computed. For the virtual VCT detector 35, the pixel pitch and the total number of pixels in both the "y" and "z" directions are selected. As shown in FIG. 6, for the virtual VCT detector 35, the total number of pixels in the "y" direction is 2J+1 and the total number of pixels in the "z" direction is 2K+1. For each (j,k)$^{th}$ pixel element of the virtual VCT detector 35, where j ranges from j=-J, -J+1, . . . , -1,0,1, . . . , J-1, J and k ranges from k=-K, -K+1, . . . , -1,0,1, . . . , K-1, K, the coordinates of each pixel on the virtual VCT detector are given by:

$$x_v = -M \cos(\theta_j) + j\Delta_y \sin(\theta_j)$$

$$y_v = M \sin(\theta_j) + j\Delta_y \cos(\theta_j)$$

$$z_v = k\Delta_z$$

Once these coordinates have been calculated, the coordinates of the intersection point ($X_d$, $Y_d$, $Z_d$) on the tomosyn thesis detector 25 of a line joining a VCT detector pixel ($X_v$, $Y_v$, $Z_v$) to the X-ray tube are computed as follows:

$$x_d = -M$$

$$y_d = y_s + \frac{(y_v - y_s)(D + x_s)}{(x_s - x_d)}$$

$$z_d = z_s + \frac{(z_v - z_s)(D + x_s)}{(x_s - x_d)}$$

Having determined which virtual pixels of the virtual VCT detector 35 correspond to which coordinates on the tomosynthesis detector 25 for each location of the source 26, the intensity values of the virtual pixels of the virtual VCT detector 35 can be determined. In order to make this determination, the projection value at coordinate $X_d$, $Y_d$, $Z_d$) on the tomosynthesis detector 25 is first computed by interpolating between the intensity values of the nearest pixels on the tomosynthesis detector 25. Those skilled in the art will understand the manner in which the intensity values can be interpolated. One way in which this can be accomplished is simply by performing a weighted averaging of the intensity values of the nearest pixels to coordinate $X_d$, $Y_d$, $Z_d$), wherein the nearest pixels are given greater weights than those that are farther away. Other interpolation techniques can be used as well, as will be understood by those skilled in the art.

The interpolated intensity values are then assigned to the corresponding virtual pixels of the virtual VCT detector 35. Once the projection data has been transformed into VCT data in this manner, a known VCT reconstruction algorithm can be used to reconstruct a 3-D image of the object being imaged. Transforming the projection data from the tomosynthesis detector 25 onto the virtual VCT detector 35 enables a VCT image reconstruction method to be applied for limited angular rotation (i.e., less than 360°) of the gantry. A variety of VCT reconstruction algorithms are known that are suitable for this purpose. For example, the well known Feldkamp reconstruction algorithm is suitable for this purpose. The Feldkamp algorithm is disclosed in an article entitled "Practical Cone-Beam Algorithm," by L. Feldkamp, L. Davis and J. Kress, J. Opt. Soc. Am., A/Vol. 1, No. 6, June 1984, which is incorporated herein by reference. This algorithm is also disclosed in a text book entitled "Principles of Computerized Tomographic Imaging", by A. Kak and M. Slaney, which is also incorporated herein by reference. The present invention is not limited with respect to the reconstruction algorithm that is utilized for this purpose.

Figure 8:
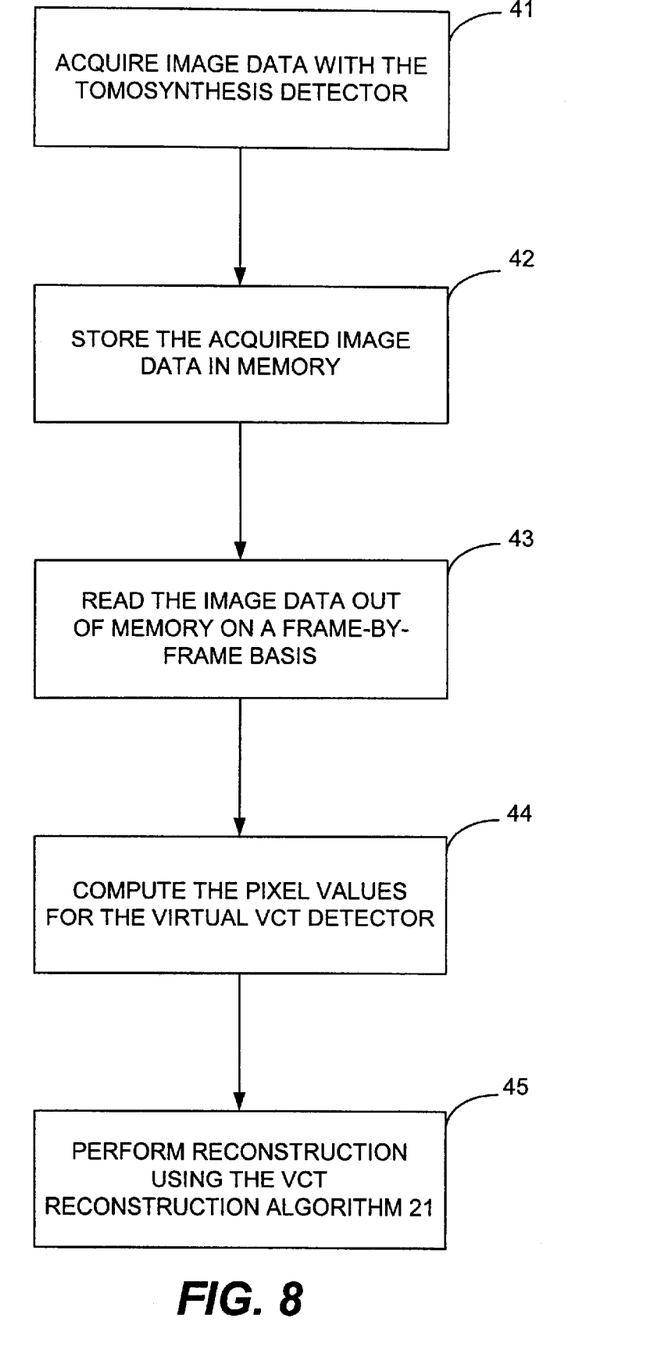
FIG. 8 is a flow chart illustrating the method of the invention in accordance with the preferred embodiment of the invention.

FIG. 8 is a flow chart illustrating the method of the present invention in accordance with the preferred embodiment. The first step in the method is to acquire image data using the tomosynthesis detector 25, as indicated by block 41. The acquired image data is then stored in memory, as indicated by block 42. The image data is then read out of memory on a frame-by-frame basis, as indicated by block 43. The intensity values for all of the pixels of the rotated virtual VCT detector 35 are then computed in the aforementioned manner, as indicated by block 44. VCT reconstruction is then performed on the transformed data by using a VCT reconstruction algorithm, as indicated by block 45.

As stated above, the well known Feldkamp reconstruction algorithm can be used for this purpose. However, the Feldkamp algorithm will need to be modified to take into account the fact that data is not acquired 360° around the object being imaged, but is only acquired for a limited range of angles. Also, sometimes the gantry rotation angles are not precisely uniformly separated, which generally depends on the tomosynthesis system that is used. Persons skilled in the art will understand how the Feldkamp algorithm or other VCT reconstruction algorithms can be modified to process data for a limited range of angles. Persons skilled in the art will also understand how to account for any non-uniformity in the separation of the gantry rotation angles.

It should also be noted that the tomosynthesis system of the present invention is not limited to any particular type or configuration of a tomosynthesis system. Also, the present invention is not limited to any particular computer for performing the processing tasks of the invention. The term "computer", as that term is used herein, is intended to denote any machine capable of performing the calculations, or computations, necessary to perform the tasks of the invention. The term "computer" is intended to denote any machine that is capable of accepting a structured input and of processing the input in accordance with prescribed rules to produce an output.

Although the method of the present invention preferably is performed by a combination of hardware and software (e.g., a microprocessor executing the transformation and reconstruction algorithms 10 and 21), it should be noted that the method of the present invention could also be performed solely in hardware, as will be understood by those skilled in the art. It should also be noted that it is not required that the computer that executes the transformation and back projection reconstruction algorithms be the same computer that controls the data acquisition process. Separate computers may be used for these functions. Those skilled in the art will also understand that the invention is not limited to the embodiments discussed above with reference to FIGS. 1–8. Those skilled in the art will understand that modifications can be made to the embodiments discussed above that are within the scope of the invention. It should also be noted that, although the invention has been discussed with reference to imaging a patient, the invention is also applicable to industrial uses, such as, for example, imaging printed circuit boards.

What is claimed is:

1. An apparatus for reconstructing an image of an object from a plurality of x-ray projection images of the object, the x-ray projection images being acquired by a tomosynthesis system, the tomosynthesis system comprising an x-ray source and a tomosynthesis detector, the x-ray source projecting x-rays through the object, the tomosynthesis detector detecting x-rays that pass through the object, the tomosynthesis detector comprising a plurality of pixels, each pixel having an intensity value associated therewith, the tomosynthesis detector generating projection data in response to the x-rays impinging thereon, the projection data corresponding to the intensity values, the tomosynthesis system producing motion of the x-ray source with respect to the object, the apparatus comprising:

logic configured to receive the projection data generated by the tomosynthesis detector, said logic being configured to project the projection data generated by the tomosynthesis detector onto a virtual computed tomography (CT) detector, the virtual CT detector comprising a plurality of virtual pixels, said logic determining intensity values for the virtual pixels based on the intensity values associated with the pixels of the tomosynthesis detector, and wherein said logic performs a CT reconstruction algorithm that processes the intensity values of the virtual pixels to thereby reconstruct an image of the object.

2. The apparatus of claim 1, wherein said logic is a computer and wherein the computer determines the intensity values of the virtual pixels by interpolating intensity values of pixels of the tomosynthesis detector.

3. The apparatus of claim 1, wherein said logic projects the projection data onto the virtual CT detector by determining spatial coordinates of the x-ray source at particular locations of the x-ray source, by determining spatial coordinates of the virtual pixels, by associating coordinates on the tomosynthesis detector with virtual pixels of the virtual VCT detector, and by interpolating intensity values of the tomosynthesis detector pixels to compute intensity values of associated virtual pixels of the virtual VCT detector.

4. An apparatus for reconstructing an image of an object from a plurality of x-ray projection images of the object, the x-ray projection images being acquired by a tomosynthesis system, the tomosynthesis system comprising an x-ray source and a tomosynthesis detector, the x-ray source projecting x-rays through the object, the tomosynthesis detector detecting x-rays that pass through the object, the tomosynthesis detector comprising a plurality of pixels, each pixel having an intensity value associated therewith, the tomosynthesis detector generating projection data in response to the x-rays impinging thereon, the projection data corresponding to the intensity values, the tomosynthesis system producing rotational motion of the x-ray source with respect to the object over a particular angular range that is less than 360°, the apparatus comprising:

logic configured to receive the projection data generated by the tomosynthesis detector, said logic being configured to project the projection data generated by the tomosynthesis detector onto a virtual computed tomography (CT) detector, the virtual CT detector comprising a plurality of virtual pixels, said logic determining intensity values for the virtual pixels based on the intensity values associated with the pixels of the tomosynthesis detector, and wherein said logic performs a CT reconstruction algorithm that processes the intensity values of the virtual pixels to thereby reconstruct an image of the object.

5. The apparatus of claim 4, wherein said logic is a computer and wherein the computer determines the intensity values of the virtual pixels by interpolating intensity values of pixels of the tomosynthesis detector.

6. The apparatus of claim 4, wherein said logic projects the projection data onto the virtual CT detector by determining spatial coordinates of the x-ray source at particular locations of the x-ray source, by determining spatial coordinates of the virtual pixels, by associating coordinates on the tomosynthesis detector with virtual pixels of the virtual VCT detector, and by interpolating intensity values of the tomosynthesis detector pixels to compute intensity values of associated virtual pixels of the virtual VCT detector.

7. A tomosynthesis system for reconstructing an image of an object from a plurality of x-ray projection images of the object, the x-ray projection images being acquired by the tomosynthesis system, the tomosynthesis system comprising:

an x-ray source, the x-ray source projecting x-rays through the object;

a tomosynthesis detector, the tomosynthesis detector detecting x-rays that pass through the object, the tomosynthesis detector comprising a plurality of pixels, each pixel having an intensity value associated therewith, the tomosynthesis detector generating projection data in response to the x-rays impinging thereon, the projection data corresponding to the intensity values, the tomosynthesis system producing motion of the x-ray source with respect to the object; and a computer, the computer receiving the projection data generated by the tomosynthesis detector, the computer being configured to project the projection data generated by the tomosynthesis detector onto a virtual computed tomography (CT) detector, the virtual CT detector comprising a plurality of virtual pixels, the computer determining intensity values for the virtual pixels based on the intensity values associated with the pixels of the tomosynthesis detector, and wherein the computer performs a CT reconstruction algorithm that processes the intensity values of the virtual pixels to thereby reconstruct an image of the object.

8. The tomosynthesis system of claim 7, wherein the computer determines the intensity values of the virtual pixels by interpolating intensity values of pixels of the tomosynthesis detector.

9. The tomosynthesis system of claim 7, wherein the computer projects the projection data onto the virtual CT detector by determining spatial coordinates of the x-ray source at particular locations of the x-ray source, by determining spatial coordinates of the virtual pixels, by associating coordinates on the tomosynthesis detector with virtual pixels of the virtual VCT detector, and by interpolating intensity values of the tomosynthesis detector pixels to compute intensity values of associated virtual pixels of the virtual VCT detector.

10. A tomosynthesis system for reconstructing an image of an object from a plurality of x-ray projection images of the object, the x-ray projection images being acquired by the tomosynthesis system, the tomosynthesis system comprising:

an x-ray source, the x-ray source projecting x-rays through the object;
a tomosynthesis detector, the tomosynthesis detector detecting x-rays that pass through the object, the tomosynthesis detector comprising a plurality of pixels, each pixel having an intensity value associated therewith, the tomosynthesis detector generating projection data in response to the x-rays impinging thereon, the projection data corresponding to the intensity values, the tomosynthesis system producing rotational motion of the x-ray source with respect to the object over a particular angular range that is less than 360°; and
a computer, the computer receiving the projection data generated by the tomosynthesis detector, the computer being configured to project the projection data generated by the tomosynthesis detector onto a virtual computed tomography (CT) detector, the virtual CT detector comprising a plurality of virtual pixels, the computer determining intensity values for the virtual pixels based on the intensity values associated with the pixels of the tomosynthesis detector, and wherein the computer performs a CT reconstruction algorithm that processes the intensity values of the virtual pixels to thereby reconstruct an image of the object.

11. The tomosynthesis system of claim 10, wherein the computer determines the intensity values of the virtual pixels by interpolating intensity values of pixels of the tomosynthesis detector.

12. The tomosynthesis system of claim 10, wherein the computer projects the projection data onto the virtual CT detector by determining spatial coordinates of the x-ray source at particular locations of the simulated movement of the x-ray source, by determining spatial coordinates of the virtual pixels, by associating coordinates on the tomosynthesis detector with virtual pixels of the virtual VCT detector, and by interpolating intensity values of the tomosynthesis detector pixels to compute intensity values of associated virtual pixels of the virtual VCT detector.

13. A method for reconstructing an image of an object from x-ray projection data, the method comprising the steps of:

acquiring the x-ray projection data with a tomosynthesis system, the tomosynthesis system comprising an x-ray source and a tomosynthesis detector, the tomosynthesis detector comprising a plurality of pixels, each pixel having an intensity value, the x-ray source projecting x-rays through an object being imaged, the tomosynthesis detector detecting x-rays that pass through the object, the detector generating the projection data in response to the x-rays impinging thereon, the tomosynthesis system producing motion of the x-ray source with respect to the object;
projecting the projection data generated by the tomosynthesis detector onto a virtual computed tomography (CT) detector, the virtual CT detector comprising a plurality of virtual pixels;
determining intensity values for the virtual pixels based on the intensity values associated with the pixels of the tomosynthesis detector; and
processing the intensity values of the virtual pixels in accordance with a CT reconstruction algorithm to thereby reconstruct an image of the object.

14. The method of claim 13, wherein the step of determining intensity values for the virtual pixels is performed by interpolating intensity values of pixels of the tomosynthesis detector to obtain interpolated intensity values and assigning the interpolated intensity values to corresponding virtual pixels of the virtual CT detector.

15. The method of claim 14, wherein the step of projecting the projection data includes the steps of:

determining spatial coordinates of the x-ray source at particular locations of the x-ray source;
determining spatial coordinates of the virtual pixels; and
associating coordinates on the tomosynthesis detector with virtual pixels of the virtual VCT detector.

16. A method for reconstructing an image of an object from x-ray projection data, the method comprising the steps of:

acquiring the x-ray projection data with a tomosynthesis system, the tomosynthesis system comprising an x-ray source and a tomosynthesis detector, the tomosynthesis detector comprising a plurality of pixels, each pixel having an intensity value, the x-ray source projecting x-rays through an object being imaged, the tomosynthesis detector detecting x-rays that pass through the object, the detector generating the projection data in response to the x-rays impinging thereon, the tomosynthesis system producing rotational motion of the x-ray source with respect to the object over a particular angular range that is less than 360°;
projecting the projection data generated by the tomosynthesis detector onto a virtual computed tomography (CT) detector, the virtual CT detector comprising a plurality of virtual pixels;
determining intensity values for the virtual pixels based on the intensity values associated with the pixels of the tomosynthesis detector; and
processing the intensity values of the virtual pixels in accordance with a CT reconstruction algorithm to thereby reconstruct an image of the object.

17. The method of claim 16, wherein the step of determining intensity values for the virtual pixels is performed by interpolating intensity values of pixels of the tomosynthesis detector to obtain interpolated intensity values and assigning the interpolated intensity values to corresponding virtual pixels of the virtual CT detector.

18. The method of claim 17, wherein the step of projecting the projection data includes the steps of:

determining spatial coordinates of the x-ray source at particular locations of the tomosynthesis detector;

determining spatial coordinates of the virtual pixels; and associating coordinates on the tomosynthesis detector with virtual pixels of the virtual VCT detector.

19. A computer program for reconstructing an image of an object from x-ray projection data, the projection data being acquired by a tomosynthesis system, the tomosynthesis system comprising an x-ray source and a tomosynthesis detector, the x-ray source projecting x-rays through the object, the tomosynthesis detector detecting x-rays that pass through the object, the tomosynthesis detector comprising a plurality of pixels, each pixel having an intensity value associated therewith, the tomosynthesis detector generating projection data in response to the x-rays impinging thereon, the projection data corresponding to the intensity values, wherein the tomosynthesis system produces motion of the x-ray source with respect to the object, the program being embodied on a computer-readable medium, the program comprising:

a first routine, the first routine projecting the projection data generated by the tomosynthesis detector onto a virtual computed tomography (CT) detector, the virtual CT detector comprising a plurality of virtual pixels;

a second routine, the second routine determining intensity values for the virtual pixels based on the intensity values associated with the pixels of the tomosynthesis detector; and a third routine, the third routine processing the intensity values of the virtual pixels in accordance with a CT reconstruction algorithm to thereby reconstruct an image of the object.

20. The computer program of claim 19, wherein the first routine comprises:

a first code segment, the first code segment determining spatial coordinates of the x-ray source at particular locations of the x-ray source;

a second code segment, the second code segment determining spatial coordinates of the virtual pixels and of the pixels of the tomosynthesis detector; and a third code segment, the third code segment associating coordinates on the tomosynthesis detector with virtual pixels of the virtual VCT detector.

21. The computer program of claim 19, wherein said second routine comprises code that determines intensity values for the virtual pixels by interpolating intensity values of pixels of the tomosynthesis detector to obtain interpolated intensity values and by assigning the interpolated intensity values to corresponding virtual pixels of the virtual CT detector.

22. A computer program for reconstructing an image of an object from x-ray projection data, the projection data being acquired by a tomosynthesis system, the tomosynthesis system comprising an x-ray source and a tomosynthesis detector, the x-ray source projecting x-rays through the object, the tomosynthesis detector detecting x-rays that pass through the object, the tomosynthesis detector comprising a plurality of pixels, each pixel having an intensity value associated therewith, the tomosynthesis detector generating projection data in response to the x-rays impinging thereon, the projection data corresponding to the intensity values, wherein the tomosynthesis system produces rotational motion of the x-ray source with respect to the object over a particular angular range that is less than 360°, the program being embodied on a computer-readable medium, the program comprising:

a first routine, the first routine projecting the projection data generated by the tomosynthesis detector onto a virtual computed tomography (CT) detector, the virtual CT detector comprising a plurality of virtual pixels;

a second routine, the second routine determining intensity values for the virtual pixels based on the intensity values associated with the pixels of the tomosynthesis detector; and a third routine, the third routine processing the intensity values of the virtual pixels in accordance with a CT reconstruction algorithm to thereby reconstruct an image of the object.

23. The computer program of claim 22, wherein said first routine comprises:

a first code segment, the first code segment determining spatial coordinates of the x-ray source at particular locations of the x-ray source;

a second code segment, the second code segment determining spatial coordinates of the virtual pixels and of the pixels of the tomosynthesis detector; and a third code segment, the third code segment associating coordinates on the tomosynthesis detector with virtual pixels of the virtual VCT detector.

24. The computer program of claim 19, wherein said second routine comprises code that determines intensity values for the virtual pixels by interpolating intensity values of pixels of the tomosynthesis detector to obtain interpolated intensity values and by assigning the interpolated intensity values to corresponding virtual pixels of the virtual CT detector.

* * * * *